United States Patent [19]

Lockhart et al.

[11] Patent Number: 5,338,465
[45] Date of Patent: Aug. 16, 1994

[54] AQUEOUS GELLABLE COMPOSITION WITH DELAYED GELLING TIME

[75] Inventors: Thomas P. Lockhart, Lodi; Paola Albonico, Milan, both of Italy

[73] Assignees: Eniricerche S.p.A.; Agip S.p.A., both of Milan, Italy

[21] Appl. No.: 853,839

[22] Filed: Mar. 19, 1992

[30] Foreign Application Priority Data

Mar. 28, 1991 [IT] Italy .................. MI.91-A/000858

[51] Int. Cl.$^5$ .............................. E21B 33/13
[52] U.S. Cl. ........................ 252/8.551; 523/130; 166/295
[58] Field of Search ........... 525/360; 523/130; 166/295; 252/8.551

[56] References Cited

U.S. PATENT DOCUMENTS

| | | | |
|---|---|---|---|
| 4,552,217 | 11/1985 | Wu et al. | 252/8.554 X |
| 4,636,572 | 1/1987 | Hudson et al. | 252/8.554 X |
| 4,683,949 | 8/1987 | Sydansk et al. | 166/295 X |
| 4,770,245 | 9/1988 | Sydansk | 166/295 |
| 4,917,186 | 4/1990 | Mumallah | 166/295 |
| 5,010,954 | 4/1991 | Falk | 166/295 |
| 5,069,281 | 12/1991 | Tackett, Jr. | 166/295 |
| 5,100,932 | 3/1992 | Lockhart et al. | 166/295 X |
| 5,131,469 | 7/1992 | Lockhart et al. | 166/295 |

FOREIGN PATENT DOCUMENTS 0383337 8/1990 European Pat. Off. .
0390279 10/1990 European Pat. Off. .
0390282 10/1990 European Pat. Off. .
2187773 9/1987 United Kingdom .

Primary Examiner—Gary Geist
Attorney, Agent, or Firm—Oblon, Spivak, McClelland, Maier & Neustadt

[57] ABSTRACT

An aqueous gellable composition having a delayed gelling time presettable within wide time and temperature ranges, contains a water-soluble organic polymer crosslinkable with chrome ion and a crosslinking/retardant system definable by the formula:

$$Cr(L)_m \cdot nL'$$

wherein:
- Cr is a trivalent chrome ion;
- L is an organic ligand consisting of a monocarboxylate or dicarboxylate ion, optionally bearing one or more amino or hydroxy functional group(s), in form complexed with chrome ion;
- L' is an organic ligand consisting of a monocarboxy or dicarboxy acid, optionally bearing one or more amino or hydroxy functional group(s), in form not complexed with chrome ion;
- m has a value comprised within the range of from 1 to 3, depending on the nature of the ligand L;
- n has a value comprised within the range of from 0.5 to 100;

with the proviso that in the crosslinking/retardant system, the ligand L is different from the ligand L'.

22 Claims, 2 Drawing Sheets

1

AQUEOUS GELLABLE COMPOSITION WITH DELAYED GELLING TIME

FIELD OF THE INVENTION

The present invention relates to an aqueous gellable composition having a delayed gelling time within wide time and temperature ranges, useful to modify the permeability of high-permeability regions in petroleum reservoirs, in particular high-temperature petroleum reservoirs.

The invention relates also to a process for reducing the permeability of a reservoir, which process uses said gellable composition.

BACKGROUND OF THE INVENTION

It is well-known that at the end of the primary step of recovery of petroleum from a petroleum reservior, in which step the recovery occurs thanks to the natural energy stored in the petroleum reservoir, or with the use of mechanical energy, inside the reservoir still a large amount of petroleum remains. Therefore, in order to increase the amount of petroleum which can be extracted, techniques of secondary recovery are customarily used, which essentially consist in injecting into the reservoir a fluid, generally water or an aqueous polymeric solution, or a gas, such as carbon dioxide or steam, which conveys petroleum to the production well.

However, owing to the heterogeneity of the petroleum bearing rock, which is constituted by regions with different permeability, such fluids tend to preferentially flow through the higher-permeability regions. The low-permeability regions remain hence non-fluxed, or only partially fluxed, and this matter of fact prevents the extraction of the therein contained petroleum.

A proposal of solution to overcome such a problem consists in modifying the permeability of the reservoir either completely or partially occluding the high-permeability regions, so that the flow of the fluid subsequently injected into the reservoir for the recovery of petroleum can be diverted towards the low-permeability regions.

For that purpose, one may resort to the injection into the reservoir of an aqueous solution of a gellable polymer, which can be gelled by means of a multivalent metal ion, to cause polymeric gels to be generated in situ.

In particular, the use is known in the art, of gellable compositions having delayed gelling time, which compositions generally consist of a crosslinkable polymer, such as, e.g., a polyacrylamide, a multivalent metal ion, and a ligand or sequestering agent for said multivalent metal ion. For example in European Patent Applns. Public. No. 0 390 279 and No. 0 390 282, the use is disclosed of compositions which can be gelled by means of trivalent chrome, which compositions contain, as the retardant agent, an organic ligand selected from the group consisting of the aliphatic or aromatic dicarboxy acids, or from the group consisting of the alpha-hydroxyacids or alpha-aminoacids.

In UK patent application 2,187,773, a gellable composition having a delayed gelling time is disclosed, which contains a water-soluble polymer, a crosslinking agent constituted by a complex of trivalent chrome with a carboxylate ion, particular acetate ion, and a retardant agent, generally constituted by acetic acid.

Unfortunately, such compositions known from the prior art allow delayed gelling times to be obtained, which are generally unsatisfactory for practical uses. In particular, the compositions known from the prior art are, in general, unsatisfactory when they are used to occlude large regions of a reservoir and/or regions far away from the injection well, in particular when reservoirs are processed which display high temperatures of their own, which accelerate the gelling rate, with the risk of a premature gel formation, and consequent occlusion of undesired regions.

SUMMARY OF THE INVENTION

Therefore, a purpose of the present invention is overcoming the drawbacks which affect the prior art, by means of an aqueous gellable composition, with delayed gelling time, which gelling time can be preset within wide ranges of time and temperature, useful to modify the permeability of high-permeability regions in petroleum reservoirs, in particular high-temperature reservoirs.

Another purpose of the present invention is a process for reducing the permeability of a petroleum reservoir, which process uses said composition.

Other purposes of the invention will be evident from the following disclosure and experimental examples.

In particular, the present Applicant found, according to the present invention, that some systems, which comprise two carboxylate ligands different from each other, with the first ligand being complexed with trivalent chrome ion, and the second ligand being in free form, lead to unexpectedly good results when they are used as crosslinking/retardant systems in converting gellable organic polymers into gels. In particular, these unexpectedly good results consist in that the delayed gelling time and temperature can be preset within wide ranges, as a function of the particular pair of selected ligands, and of their mutual ratio in the crosslinking/retardant system.

Figure 1:
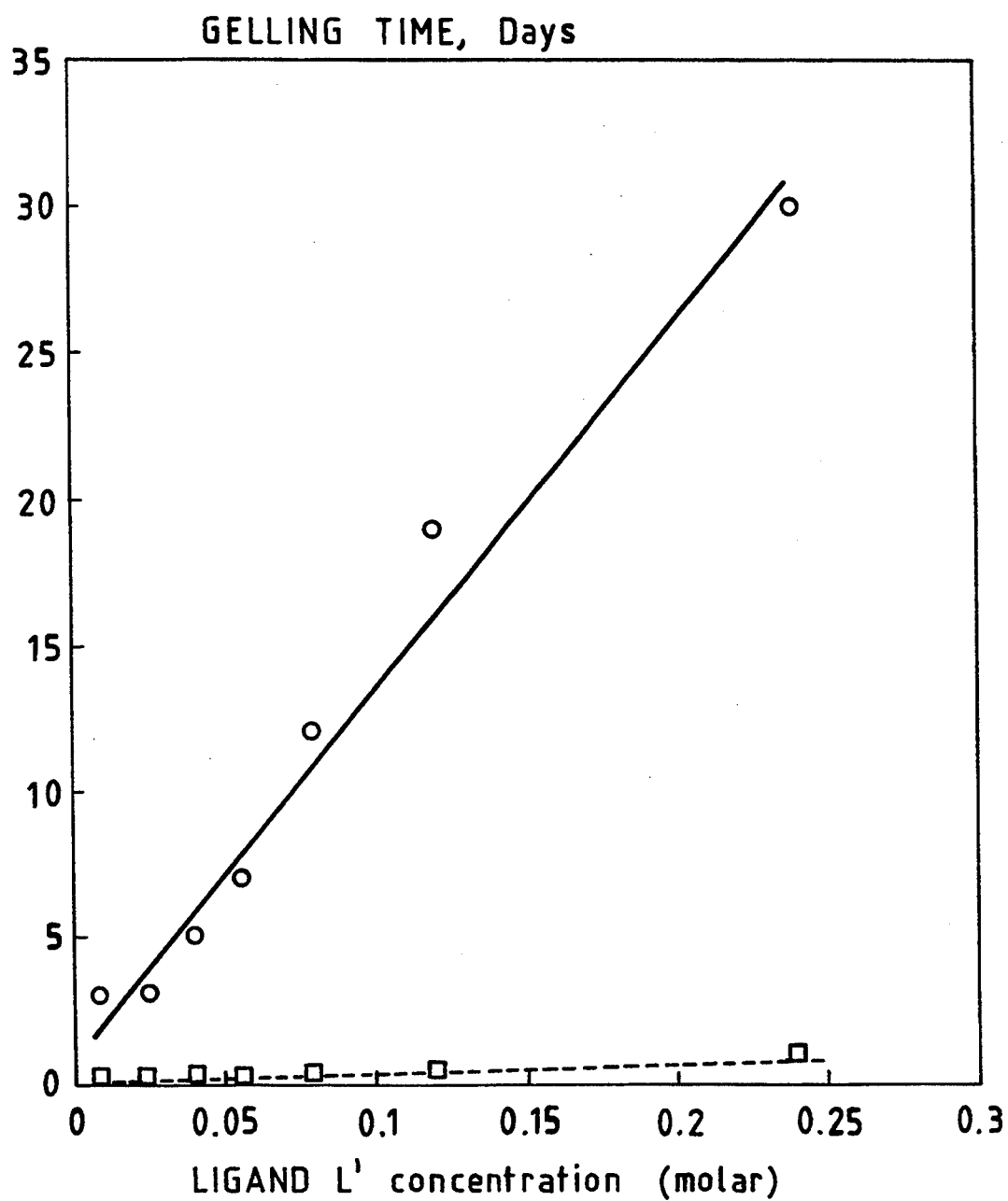
FIG. 1 displays the gelling time—L' concentration data reported in Example 10 in which the solid line relates to malonic acid and the dashed line to acetic acid used as the component L'.

In accordance therewith, according to a first aspect thereof, the present invention relates to an aqueous gallable composition with delayed gelling presettable to occur within wide time and temperature ranges, containing an organic, water-soluble polymer crosslinkable with chrome ion and a crosslinking/retardant system definable by the formula:

$$Cr(L)_m \cdot nL'$$

wherein:
- Cr is a trivalent chrome ion;
- L is an organic ligand consisting of a monocarboxylate or dicarboxylate ion, optionally bearing one or more amino or hydroxy functional group(s), in form complexed with chrome ion;
- L' is an organic ligand consisting of a monocarboxy or dicarboxy acid, optionally bearing one or more amino or hydroxy functional group(s) in form not complexed with chrome ion;

m has a value comprised within the range of from 1 to 3, depending on the nature of the ligand L;

n has a value comprised within the range of from 0.5 to 100;

with the proviso that in the crosslinking/retardant system, the ligand L is different from the ligand L'.

The water-soluble organic polymers which can be crosslinked with chrome ion, useful for the purposes of the present invention, are generally selected from the group consisting of acrylamide polymers. In particular, there can be used either acrylamide homopolymers, or acrylamide copolymers with one or more copolymerisable unsaturated monomer(s), such as, e.g., acrylic acid, methacrylamide, sodium 2-acrylamido- 2-methyl-propane-sulfonate and N-vinyl-2-pyrrolidone. Among the copolymers, the copolymers of acrylamide with sodium 2-acrylamido-2-methyl-propane-sulfonate, the copolymers of acrylamide with N-vinyl-2-pyrrolidone and the terpolymers of acrylamide with sodium 2-acrylamido-2-methyl-propane-sulfonate and N-vinyl-2-pyrrolidone, are preferably used.

Said acrylamide polymers and copolymers can be either substantially non-hydrolyzed (less than 1% of amidic groups hydrolysed into free carboxy groups), or partially hydrolyzed (more than 1% of amidic groups hydrolyzed into free carboxy groups).

The molecular weight of these acrylamide (co)polymers may generally be comprised within the range of from 100,000 to 20,000,000, and, preferably, within the range of from 200,000 to 12,000,000.

The concentration of the acrylamide (co)polymer in the gellable composition according to the present invention can generally range from 1,000 to 80,000 ppm (parts per million parts by weight), and preferably will be comprised within the range of from 3,000 to 50,000 ppm and, in the most preferred form of practical embodiment, will be comprised within the range of from 5,000 to 10,000 ppm when fresh water is used, and of from 10,000 to 30,000 when salt water is used (such as, e.g., sea water).

The acid for the ligand L and the ligand L' of the crosslinking/retardant system according to the present invention can be selected from among:

monocarboxy aliphatic acids R—COOH, wherein R is a $C_1$-$C_6$ alkyl radical; examples of aliphatic monocarboxy acids are: acetic acid, propionic acid and butyric acid;

dicarboxy aliphatic acids HOOC—$(CH_2)_a$—COOH, wherein a has a value comprised within the range of from 0 to 4, and their relevant monoesters and monoamides; examples of such aliphatic dicarboxy acids and relevant monoesters and monoamides are: malonic acid, succinic acid, glutaric acid and adipic acid;

aliphatic alpha-hydroxyacids R'—CH(OH)—COOH, in which R' is a hydrogen atom, or an alkyl or hydroxyalkyl radical containing from 1 to 6 carbon atoms in its alkyl or hydroxyalkyl moiety, and the lactones thereof; examples of such aliphatic alpha-hydroxyacids and relevant lactones are: glycolic acid, lactic acid, alpha-hydroxybutyric acid, ascorbic acid and tartaric acid;

aliphatic alpha-aminoacids R"—CH(NH_2)—COOH, wherein R" is a hydrogen atom, or an alkyl or hydroxyalkyl radical containing from 1 to 6 carbon atoms in its alkyl or hydroxyalkyl moiety; examples of such aliphatic alpha-aminoacids are: glycine, alpha-aminobutyric acid and serene;

aromatic alpha-dicarboxy acids, such as, e.g., phthalic acid; and aromatic alpha-hydroxyacids, such as, e.g., salicylic acid.

According to a preferred form of practical embodiment of the present invention, said ligands L is acetate ion or malonate ion or glycolate ion and the ligand L' is selected from among: malonic acid, ascorbic acid, glycolic acid, alpha-hydroxybutyric acid, alpha-aminobutyric acid, serine, phthalic acid and monoamide of glutaric acid.

Particularly preferred crosslinking/retardant systems according to the present invention are:

$Cr(acetate)_3$.n malonic acid, with n comprised within the range of from 0.5 to 100;

$Cr(acetate)_3$.n salycilic acid, with n comprised within the range of from 0.5 to 50;

$Cr(acetate)_3$.n ascorbic acid, with n comprised within the range of from 0.5 to 100;

$Cr(malonate)_3$.n salycilic acid, with n comprised within the range of from 0.5 to 50; and $Cr(glycolate)_3$.n malonic acid, with n comprised within the range of from 0.5 to 100;

$Cr(malonate)_3$.n glycolic acid, with n comprised within the range of from 0.5 to 100.

The crosslinking/retardant system according to the present invention can additionally contain one or more hydroxy ions and/or neutral molecules, such as, e.g., water or pyridine, and other monovalent and divalent inorganic ions, generally $Na^+$ and $K^+$, suitable for balancing the charge of the same system.

In the crosslinking/retardant system according to the present invention, the molar ratio of the ligand L' to chrome is selected as a function of the particular pair of ligands selected and of the value of the gelling delay which one wishes to obtain, also on considering the temperature of the region of reservoir to be occluded. As indicated above, such a ratio can generally be comprised within the range of from 0.5 to 100, with preferred values ranging from 0.5 to 50.

The amount of crosslinking/retardant system contained in the gellable compositions according to the present invention will be that amount which makes it possible a concentration of chrome ion to be obtained in said composition, which is comprised within the range of from 10 to 5,000 ppm, and preferably within the range of from 25 to 800 ppm, with most preferred values being of from 100 to 600 ppm (parts per million parts by weight).

The gellable composition of the present invention can additionally contain one or more stabilizer agent(s) for the polymer, as customarily used, e.g., thiourea.

Furthermore, the gellable composition according to the present invention will have a pH value comprised within the range of gelation of the same composition, which can be comprised within the range of from about 2 to about 9, and preferably is of the order of from 4 to 7. Therefore, when either necessary or desired, the pH value of the composition will be adjusted by means of the addition of a mineral acid or base, as needed. A mineral acid suitable for that purpose is, e.g., hydrochloric acid, and a suitable base is, e.g., sodium hydroxide.

The aqueous gellable composition according to the present invention can be prepared by simply blending its components, on considering that the sequence of addition is not critical.

However, preferably, an aqueous solution is prepared first, which contains the polymer and the optional stabilizer agent, then an aqueous solution of the ligand L' is added to the solution of the polymer, and then the solution of the complex of trivalent chrome with the ligand L is added.

This complex can be prepared by means of known techniques, such as described, e.g., in "Inorganic Syntheses", Vol. 16, pages 80–81, and in "Comprehensive Inorganic Chemistry", Pergamon Press (Oxford), Vol. 3 (1973), pages 627–700.

Water used in the composition can be free from salts, or it can contain salts and, advantageously, the same water contained in the same reservoir can be used.

According to another purpose thereof, the present invention relates to a process for reducing the permeability in a petroleum reservoir, which process uses the gellable composition disclosed hereinabove.

More particularly, said process comprises the following steps:

(a) preparing an aqueous gellable composition, as disclosed hereinabove;

(b) injecting said gellable composition into the petroleum reservoir through at least one well;

(c) causing said composition to flow through the reservoir, until it reaches and substantially fills the high-permeability region which has to be treated; and (d) causing said composition to turn into a gel, with the permeability of the above said region being consequently decreased.

The use of the gellable composition makes it advantageously possible the permeability high-permeability regions situated deeply in the reservoir, where the temperature is higher, or anyway far away from the injection well, to be reduced, without that an early gelling occurs.

Thanks to the use of a free ligand and a complexed ligand, different from each other, the gelling time can be preset within a very wide range, by properly selecting the pair of ligands and their mutual ratio. A further possibility of regulation of the gelling time is given by the ageing time of the complex formed by trivalent chrome ion and ligand L. More particularly, in case of acetate ion, it was found that to longer ageing times of the same complex, shorter gelling times correspond, with the other conditions being the same. In any case, it was found that the use of two different ligands in a same crosslinking/retardant system is essential in order to attain the benefits of the instant invention. These benefits cannot be obtained, e.g., by using the chrome acetate/acetic acid system according to the prior art.

Finally, the use of two different ligands favors the selection of at least one cheap ligand, what makes it possible economic advantages to be accomplished, or a complex $Cr(L)_m$ available from the market, or easy to be prepared, to be used in combination with a ligand L', so as to accomplish good redardant performances.

The compositions according to the present invention turn into a gel with useful delayed-gelation times within a wide range of temperatures, such as from room temperature up to 120° C. or more. In general, the present Applicant found that delays of up to one month, or even more, can be accomplished, by operating at temperatures of the order of from 90° to 120° C.

EXAMPLES ILLUSTRATING THE INVENTION

The invention is further illustrated by the following experimental examples.

EXAMPLE 1

Use of the crosslinking/retardant system:

$Cr(acetate)_3 . 7 L'$ wherein:
L' = acetic acid (for comparative purposes), monoamide of glutaric acid, phthalic acid, glycolic acid, salicylic acid or ascorbic acid.

In this example, as the water-soluble, gellable organic polymer, a commercial copolymer of acrylamide and a sodium 2-acrylamido-2-methyl-1-propane-sulfonate in weight ratio of approximately 72:25, with about 4% of hydrolyzed amidic groups to yield carboxy groups, is used. An aqueous solution of the copolymer is prepared, and thiourea is added to it, to perform the function of stabilizer agent.

An aqueous solution is prepared of $Cr(acetate)_3 . H_2O$ complex is prepared, and the solution is allowed to age 2 days before use.

The aqueous, gellable compositions are prepared by mixing, in a test tube provided with screw-threaded cap, the solution of the copolymer and stabilizer agent, with the aged aqueous solution of $Cr(acetate)_3 . H_2O$ complex, and subsequently adding the ligand L' (optionally as its alkali-metal salt), dissolved in water. The pH value of the resulting solution is adjusted at the value of 5±0.1, with aqueous sodium hydroxide, or aqueous hydrochloric acid, according to as needed.

In particular, the resulting composition contains 5,000 ppm (parts per million parts by weight) of copolymer, 5,000 ppm of thiourea and 600 ppm of trivalent chrome. The concentration of the ligand L' is, in any case, of 0.08M (molar ratio of L'/Cr =7:1).

The so prepared compositions are submitted to gelation by being kept in an oil bath at 120° C. for 15 minutes, and being then charged to an oven at 120° C. The so obtained gelling times are reported in following Table I.

TABLE I

| Ligand L' | Gelling time (hours) |
|---|---|
| Acetic acid | 1 |
| Monoamide of glutaric acid | 3.3 |
| Phthalic acid | 43 |
| Glycolic acid | 46–115.5 |
| Salicylic acid | 50 |
| Ascorbic acid | 53–124 |

EXAMPLE 2

Use of the crosslinking/retardant system:

$Cr(CH_3COO)_3 . 7 L'$ wherein:
L' = acetic acid (for comparative purposes), L-serine, alpha-hydroxybutyric acid, lactic acid, 2-aminobutyric acid, glycolic acid, salicylic acid, malonic acid, ascorbic acid.

In this example, as the water-soluble, gellable organic polymer, a commercial copolymer of acrylamide and sodium 2-acrylamido-2-methyl-1-propane-sulfonate in , a weight ratio of approximately 57:43, with about 6% of amidic groups hydrolyzed to yield carboxy groups, is used.

An aqueous solution of $Cr(acetate)_3.H_2O$ complex is prepared, and the solution is used 1–3 days later.

By operating as in Example 1, aqueous, gellable compositions are prepared with a pH value of $5\pm0.1$, which contain 5,000 ppm (parts per million parts by weight) of copolymer, 5,000 ppm of thiourea and 600 ppm of trivalent chrome. The concentration of the ligand L' is, in any case, of 0.08M (molar ratio of L'/Cr=7:1).

The so prepared compositions are submitted to gelation by being kept in an oil bath at 90°–95° C. for 15 minutes, and being then charged to an oven at 120° C. The so obtained gel ling times are reported in following Table II.

TABLE II

| Ligand L' | Gelling time |
| --- | --- |
| Acetic acid | 3.8 hours |
| L-serine | 8–18 hours |
| alpha-Hydroxybutyric acid | 8–18 hours |
| Lactic acid | 30–45 hours |
| alpha-Aminobutyric acid | 26–40 hours |
| Glycolic acid | 48–52 hours |
| Salicylic acid | 3–6 days |
| Malonic acid | 3–6 days |
| Ascorbic acid | 8–9 days |

EXAMPLE 3

Use of the crosslinking/retardant system:

$Cr(acetate)_3$.n malonic acid with n comprised within the range of from 2 to 7.

By operating as in the preceding Examples, aqueous, gellable compositions are prepared with a pH value of $5\pm0.1$, which contain 5,000 ppm (parts per million parts by weight) of the copolymer of Example 1, 5,000 ppm of thiourea and 600 ppm of trivalent chrome.

In this example, the aqueous solution of $Cr(acetate)_3.H_2O$ complex is aged for 2 days.

The concentration of the ligand L' (malonic acid) in the composition is varied within the range of from 0.024 to 0.080M, so as to have molar ratios of malonic acid/chrome comprised within the range of from 2:1 to 7:1.

The so prepared compositions are submitted to gelation by being kept in an oil bath at 120° C. for 15 minutes, and being then charged to an oven at 120° C. The so obtained gelling times are reported in following Table III.

TABLE III

| Concentration of malonic acid | Ratio of malonic acid:chrome | Gelling time |
| --- | --- | --- |
| 0.024 M | 2:1 | 22 hours |
| 0.040 M | 3.5:1 | 198 ± 12 hours |
| 0.056 M | 5:1 | 354 ± 24 hours |
| 0.080 M | 7:1 | 24–27 days |

EXAMPLE 4

Use of the crosslinking/retardant system:

$Cr(acetate)_3$.n salicylic acid with n comprised within the range of from 2 to 7.

By operating as in the preceding Examples, aqueous, gellable compositions are prepared with a pH value of $5\pm0.1$, which contain 5,000 ppm (parts per million parts by weight) of the copolymer of Example 1, 5,000 ppm of thiourea and 600 ppm of trivalent chrome.

In this example, the aqueous solution of $Cr(acetate)_3.H_2O$ complex used as soon as it is ready.

The concentration of the ligand L' (salicylic acid) in the composition varied within the range of from 0.024 to 0.080M, so as to have molar ratios of salicylic acid/chrome comprised within the range of from 2:1 to 7:1.

The so prepared compositions are submitted to gelation by being kept in an oil bath at 120° C. for 15 minutes, and being then charged to an oven at 120° C. The so obtained gelling times are reported in following Table IV.

TABLE IV

| Concentration of salicylic acid | Ratio of salicylic acid:chrome | Gelling time |
| --- | --- | --- |
| 0.024 M | 2:1 | 4 hours |
| 0.040 M | 3.5:1 | 30 hours |
| 0.056 M | 5:1 | 132 ± 32 hours |
| 0.080 M | 7:1 | 200 ± 12 hours |

EXAMPLE 5

Use of the crosslinking/retardant system:

$Cr(acetate)_3$.n ascorbic acid with n comprised within the range of from 0.7 to 7.

By operating as in the preceding Examples, aqueous, gellable compositions are prepared with a pH value of $5\pm0.1$, which contain 5,000 ppm (parts per million parts by weight) of the copolymer of Example 1, 5.000 ppm of thiourea and 600 ppm of trivalent chrome.

In this example, the aqueous solution of $Cr(acetate)_3.H_2O$ complex is used 1 day after its preparation.

The concentration of the ligand L' (ascorbic acid) in the composition is varied within the range of from 0.008 to 0.080M, so as to have molar ratios of ascorbic acid/chrome comprised within the range of from 0.7:1 to 7:1.

The so prepared compositions are submitted to gelation by being kept in an oil bath at 120° C. for 15 minutes, and being then charged to an oven at 120° C. The so obtained gelling times are reported in following Table V.

TABLE V

| Concentration of ascorbic acid | Ratio of ascorbic acid:chrome | Gelling time |
| --- | --- | --- |
| 0.008 M | 0.7:1 | 2 hours |
| 0.024 M | 2:1 | 112 ± 33 hours |
| 0.040 M | 3.5:1 | 112 ± 33 hours |
| 0.056 M | 5:1 | 159 ± 8 hours |
| 0.080 M | 7:1 | 278 ± 32 hours |

The tests are repeated by using an aqueous solution of $Cr(acetate)_3.H_2O$ complex, aged for 1 month. The results are reported in following Table VI.

TABLE VI

| Concentration of ascorbic acid | Ratio of ascorbic acid:chrome | Gelling time |
| --- | --- | --- |
| 0.024 M | 2:1 | 2 hours |
| 0.040 M | 3.5:1 | 5 ± 1 hours |
| 0.056 M | 5:1 | 7–22 hours |
| 0.080 M | 7:1 | 54 hours |
| 0.160 M | 14:1 | 10 ± 2 days |
| 0.240 M | 30:1 | 17 ± 2 days |

EXAMPLE 6

Use of the crosslinking/retardant system:

Cr(malonate)$_3$ · n salicylic acid with n comprised within the range of from 2 to 6.

By operating as in the preceding Examples, aqueous, gellable compositions are prepared with a pH value of 5±0.1, which contain 5,000 ppm (parts per million parts by weight) of the copolymer of Example 1, 5,000 ppm of thiourea and 200 ppm of trivalent chrome.

The Cr(malonate)$_3$ complex is prepared as described in Inorganic Syntheses, "Malonate Complexes of Chromium-(III)".

The concentration of the ligand L' (salicylic acid) in the composition is varied within the range of from 0.008 to 0.024M, so as to have molar ratios of salicylic acid/chrome comprised within the range of from 2:1 to 6:1. For comparison purposes, a test without the ligand L' is carried out.

The so prepared compositions are submitted to gelation by being kept in an oil bath at 120° C. for 15 minutes, and being then charged to an oven at 120° C. The so obtained gelling times are reported in following Table VII.

TABLE VII

| Concentration of salicylic acid | Ratio of salicylic acid:chrome | Gelling time |
| --- | --- | --- |
| 0 | — | 15 ± 8 hours |
| 0.008 M | 2:1 | 48 hours |
| 0.024 M | 6:1 | 150–165 hours |

The tests are repeated by using Cr(malonate)$_2$·n salicylic acid as the retardant crosslinking system. The results are reported in following Table VIII.

TABLE VIII

| Concentration of salicylic acid | Ratio of salicylic acid:chrome | Gelling time |
| --- | --- | --- |
| 0 | — | 26.5 hours |
| 0.008 M | 2:1 | 55–69 hours |
| 0.024 M | 6:1 | 149–165 hours |
| 0.080 M | 20:1 | 9 days |
| 0.160 M | 40:1 | 14 ± 1 days |

EXAMPLE 7

Use of the crosslinking/retardant system:

Cr(glycolate)$_3$·n malonic acid with n comprised within the range of from 2 to 10.

By operating as in the preceding Examples, aqueous, gellable compositions are prepared with a pH value of 5±0.1, which contain 5,000 ppm (parts per million parts by weight) of the copolymer of Example 1, 5,000 ppm of thiourea and 200 ppm of trivalent chrome.

The Cr(glycolate)$_3$ complex is prepared by using the procedure as described in Inorganic Syntheses, Volume 16, pages 80–81, for the preparation of complexes of Cr-(III) with malonate.

The concentration of the ligand L' (malonic acid) in the composition is varied within the range of from 0.008 to 0.04M, so as to have molar ratios of malonic acid/chrome comprised within the range of from 2:1 to 10:1.

The so prepared compositions are submitted to gelation by being kept in an oil bath at 120° C. for 15 minutes, and being then charged to an oven at 120° C.. The so obtained gelling times are reported in following Table IX.

TABLE IX

| Concentration of malonic acid | Ratio of malonic acid:chrome | Gelling time |
| --- | --- | --- |
| 0.008 M | 2:1 | 5.5–21 hours |
| 0.024 M | 6:1 | 61–85 hours |
| 0.04 M | 10:1 | 94 hours |

EXAMPLE 8

By operating as in the preceding Examples, an aqueous, gellable composition with a pH value of 5±0.1 is prepared, which contains 5,000 ppm (parts per million parts by weight) of the copolymer of Example 1, 5,000 ppm of thiourea, 600 ppm of trivalent chrome [supplied as aqueous, one-month-aged Cr(acetate)$_3$], and 0.024M ascorbic acid (molar ratio of ascorbic acid to Cr=6:1).

The gelation time of this composition, at 90° C. is of 23±1 hours.

EXAMPLE 9

By operating as in the preceding Examples, an aqueous, gallable composition with a pH value of 5±0.1 is prepared, which contains 5,000 ppm (parts per million parts by weight) of the copolymer of Example 1, 5,000 ppm of thiourea, 600 ppm of trivalent chrome [supplied as aqueous, one-month-aged Cr(acetate)$_3$], and 0.024M glycolic acid (molar ratio of glycolic acid to Cr=2:1).

The gelation time of this composition, at 90° C., is of 48–50 hours.

EXAMPLE 10

By operating as in the preceding Examples, aqueous, gallable compositions with a pH value of 5±0.1 are prepared, which contain 5,000 ppm (parts per million parts by weight) of the copolymer of Example 1, 5,000 ppm of thiourea, 400 ppm of trivalent chrome [supplied as aqueous, about-one-month-aged Cr(acetate)$_3$], and variable amounts of malonic acid.

These compositions are submitted to gelling at 120° C. and in the chart of FIG. 1 (—line) the gelling time is reported as days (on the ordinate), as a function of the molar concentration of malonic acid (on the abscissa).

For comparison purposes, compositions are prepared, which are very similar to the preceding compositions, with the difference that the crosslinking/retardant system is constituted by Cr(acetate)$_3$ and acetic acid, with variable amounts of the latter.

The data relevant to the gelation at 120° C. are reported in the chart of FIG. 1 (line - - -).

EXAMPLE 11

By operating as in the preceding Examples, aqueous, gellable compositions are prepared with a pH value of 5±0.1, which contain 5,000 ppm (parts per million parts by weight) of the copolymer of Example 1, 5,000 ppm of thiourea and 600 ppm of trivalent chrome, supplied as aqueous Cr(acetate)$_3$ aged for variable times, and salicylic acid in variable amounts.

The compositions are gelled at 120° C., and the results of this test are summarized in following Table X.

TABLE X

| Molar concentration of salicylic acid | Ageing time of the solution of Cr(acetate)₃ | Gelling time |
|---|---|---|
| 0 | 15 minutes | <15 minutes |
| 0.08 M | 15 minutes | <15 minutes |
| 0.024 M | 4 hours | 2 hours |
| 0.040 M | 30 hours | 4 hours |
| 0.056 M | 132 hours | 22 hours |
| 0.080 M | 200 hours | 62 hours |
| 0.160 M | — | 118 hours |

EXAMPLE 12

By operating as in the preceding Examples, aqueous, gellable compositions are prepared with a pH value of 5±0.1, which contain 5,000 ppm (parts per million parts by weight) of the copolymer of Example 1, 5,000 ppm of thiourea and 600 ppm of trivalent chrome, supplied as aqueous, fresh or 24-days-aged Cr(acetate)₃, and salicylic acid in variable amounts.

Figure 2:
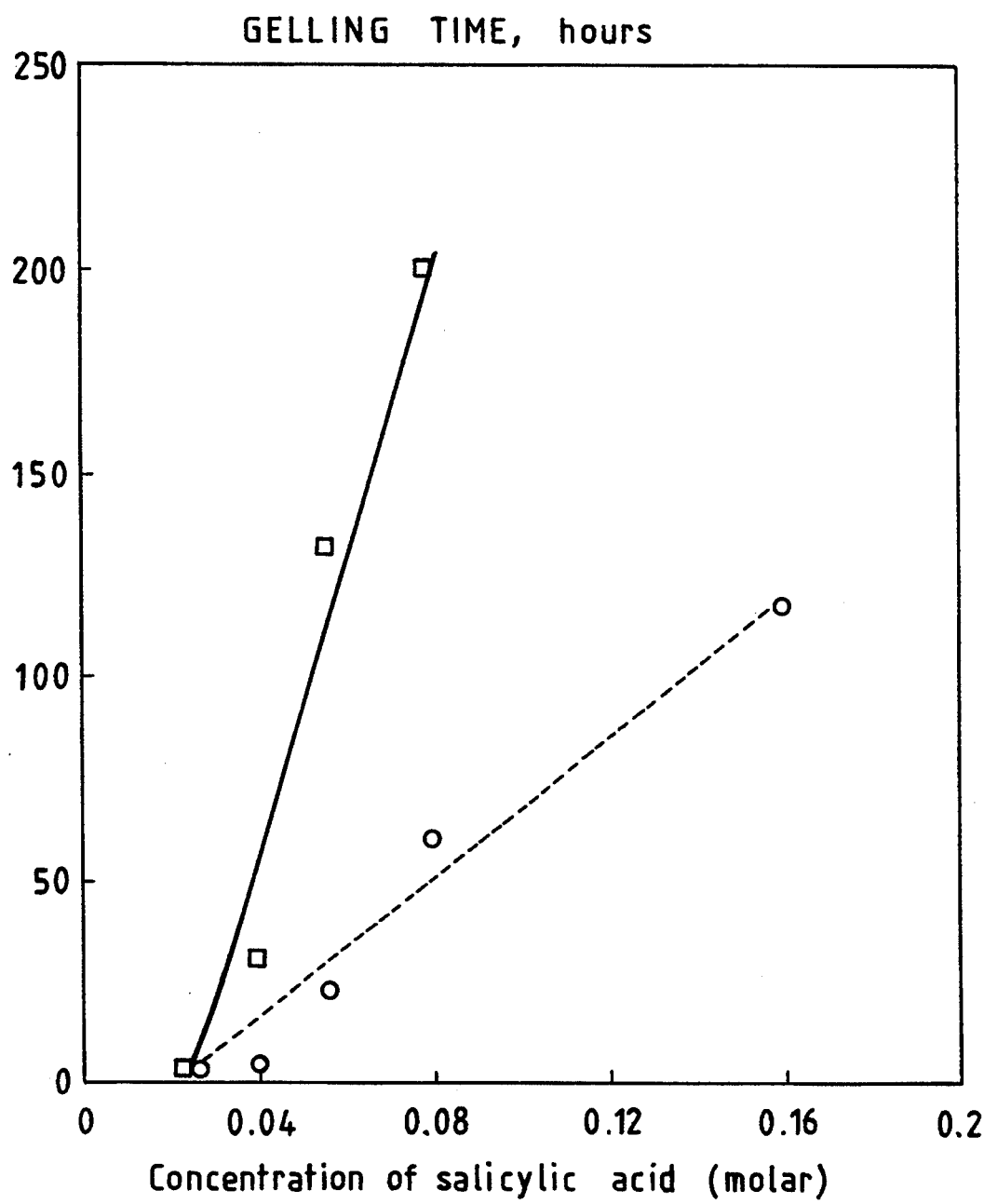
FIG. 2 displays the gelling time—salicylic acid concentration data reported in Example 12 where the solid line refers to fresh chrome acetate and the dashed time to aged chrome acetate salicylic acid solutions containing thiourea.

The compositions are gelled at 120° C., and the results are reported in the chart in FIG. 2.

In this figure, the values of molar concentration of salicylic acid in the gellable composition are reported on the abscissa, and on the ordinate the gelation time is reported as hours. In this chart, the "—" line relates to the compositions which use freshly-prepared chrome acetate and the "- - -" line relates to the compositions which use 24-hours-aged chrome acetate.

EXAMPLE 13

By operating as in the preceding Examples, aqueous, gellable compositions are prepared with a pH value of 5±0.1, which contain 5,000 ppm ( parts per million parts by weight) of the copolymer of Example 1, 5,000 ppm of thiourea and 200 ppm of trivalent chrome, supplied as aqueous Cr(malonate)₃, and glycolic acid in variable amounts, The compositions are gelled at 90° C. and 120° C. and the results are summarized in following Table XI.

TABLE XI

| Molar concentration of glycolic acid | Gelling time at 90° C. | Gelling time at 120° C. |
|---|---|---|
| 0.008 M | 117–141 hours | 29–47 hours |
| 0.024 M | 284–308 hours | 47–55 hours |
| 0.040 M | 429–453 hours | 77–142 hours |
| 0.056 M | n.d. | 142–166 hours |
| 0.080 M | 868–933 hours | 310–334 hours |
| 0.160 M | n.d. | 343–359 hours | n.d. = not determined.

EXAMPLE 14

The process is carried out as in Example 13, using 20,000 ppm (parts per million parts by weight) of copolymer of Example 1, and replacing water with synthetic sea water.

The results are reported in following Table XII.

TABLE XII

| Molar concentration of glycolic acid | Gelling time at 90° C. | Gelling time at 120° C. |
|---|---|---|
| 0.008 M | 18–42 hours | 22–46 hours |
| 0.024 M | 72–137 hours | n.d. |
| 0.040 M | 72–137 hours | 53–118 hours |
| 0.080 M | 309–333 hours | n.d. |
| 0.160 M | 356–380 hours | 166–190 hours |
| 0.240 M | 549–573 hours | 290–317 hours |
| 0.300 M | 716–740 hours | 382–406 hours | n.d. = not determined.

We claim:

1. Aqueous gellable composition containing an organic, water-soluble polymer crosslinkable with chromium ion and a crosslinking/retardant system of the formula:

$$Cr(L)_m \cdot nL'$$

wherein:
Cr is a trivalent chromium ion;
L is an organic ligand consisting of a monocarboxylate or dicarboxylate ion, optionally bearing one or more amino or hydroxy functional group(s), complexed with chromium ion;
L' is a monocarboxy or dicarboxy acid, optionally bearing one or more amino or hydroxy functional group(s), not complexed with chromium ion;
m is a number from 1 to 3;
n is a number from 0.5 to 100;
with the proviso that in the crosslinking/retardant system, the acid of which L is the ion specified is different from L'.

2. Composition according to claim 1, characterized in that in the crosslinking/retardant system, the molar ratio of L' to chromium is from 0.5:1 to 50:1.

3. Composition according to claim 1, characterized in that the concentration of chromium ion in the composition is from 10 to 5,000 ppm.

4. Composition according to claim 1, characterized in that the concentration of the water-soluble organic polymer is from 1,000 to 80,000 ppm.

5. A composition according to claim 4, wherein the water of the aqueous gellable composition is fresh water and the concentration of the water-soluble organic polymer is 5,000–10,000 ppm.

6. A composition according to claim 4, wherein the water in the aqueous gellable composition is seawater and the concentration of the water-soluble organic polymer is 10,000–30,000 ppm.

7. Composition according to claim 1, characterized in that L is acetate or malonate or glycolate ion and L' is selected from the group consisting of malonic acid, ascorbic acid, glycolic acid, alpha-hydroxybutyric acid, alpha-aminobutyric acid, serine and phthalic acid and the monoamide of glutaric acid.

8. Composition according to claim 1, characterized in that said crosslinking/retardant system is selected from the group consisting of:
Cr(acetate)₃. $n^I$ malonic acid, where $n^I$ is from 0.5 to 100;
Cr(acetate)₃.$n^{II}$ salicylic acid, where $n^{II}$ is from 0.5 to 50;
Cr(acetate)₃.$n^{III}$ ascorbic acid, where $n^{III}$ is from 0.5 to 100;
Cr(malonate)₃.$n^{IV}$ salicylic acid, where $n^{IV}$ is from 0.5 to 50;
Cr(glycolate)₃.$n^V$ malonic acid, where $n^V$ is from 0.5 to 100; and Cr(malonate)$_3$.n$^{VI}$ glycolic acid, where n$^{VI}$ is from 0.5 to 100.

9. Composition according to claim 1, characterized in that the crosslinking/retardant system additionally contains one or more hydroxy ions and/or neutral molecules, and/or other monovalent or divalent inorganic ions, suitable for balancing the charge of the same system.

10. Composition according to claim 1, characterized in that said organic polymer is selected from the group consisting of acrylamide homopolymers and acrylamide copolymers with one or more copolymerisable unsaturated monomer(s) selected from the group consisting of acrylic acid, methacrylamide, sodium 2-acrylamido-2-methyl-propane-sulfonate and N-vinyl-2-pyrrolidone, which acrylamide homopolymers or copolymers have a molecular weight of from 100,000 to 20,000,000, said acrylamide homopolymers and copolymers having less than 1% of amidic groups hydrolyzed into free carboxy groups or partially hydrolyzed having more than 1% of amidic groups but not all amidic groups hydrolyzed into free carboxy groups.

11. Composition according to claim 10, characterized in that the acrylamide copolymers are copolymers of acrylamide with sodium 2-acrylamido-2-methyl-propane-sulfonate, the copolymers of acrylamide with N-vinyl-2-pyrrolidone and the terpolymers of acrylamide with sodium 2acrylamido-2-methyl-propane-sulfonate and N-vinyl-2-pyrrolidone.

12. A composition according to claim 10, wherein the molecular weight of the acrylamide homopolymer or copolymer is 200,000–12,000,000.

13. Composition according to claim 1, having a pH value of from about 2 to about 9.

14. A composition according to claim 13, wherein the pH value is about 4 to 7.

15. Composition according to claim 1, characterized in that the acid of which L is the ion specified and L' are selected from the group consisting of:
  monocarboxy aliphatic acids R—COOH, wherein R is a $C_1$-$C_6$ alkyl radical;
  dicarboxy aliphatic acids HOOC—(CH$_2$)$_a$—COOH, wherein a is from 0 to 4, and monoesters and monoamides thereof;
  aliphatic alpha-hydroxyacids R'—CH(OH)—COOH, in which R' is a hydrogen atom, or an alkyl or hydroxyalkyl radical containing from 1 to 6 carbon atoms and the lactones thereof;
  aliphatic alpha-aminoacids R"—CH(NH$_2$)—COOH, wherein R" is a hydrogen atom, or an alkyl or hydroxyalkyl radical containing from 1 to 6 carbon atoms;
  aromatic alpha-dicarboxy acids; and
  aromatic alpha-hydroxyacids.

16. Composition according to claim 1, characterized in that the acid of which L is the specified ion and L' are selected from the group consisting of acetic acid, propionic acid butyric acid, malonic acid, succinic acid, glutaric acid adipic acid, glycolic acid, lactic acid, alpha-hydroxybutyric acid, ascorbic acid, tartaric acid, glycine, alpha-aminobutyric acid, serine, phthalic acid, and salicylic acid.

17. Composition according to claim 1, which additionally contains one or more stabilizer agent(s) for the polymer.

18. A composition according to claim 17, wherein the stabilizer is thiourea.

19. Process for reducing the permeability in a petroleum reservoir, which process comprises the following steps:
  (a) preparing an aqueous gellable composition of the composition defined in claim 1;
  (b) injecting said gellable composition into the petroleum reservoir through at least one well;
  (c) causing said composition to flow through the reservoir, until it reaches and substantially fills the high-permeability region which has to be treated; and
  (d) causing said composition to turn into a gel, with the permeability of the above said region being consequently decreased.

20. A composition according to claim 1, characterized in that the concentration of chromium ion in the composition is from 25 to 800 ppm.

21. A composition according to claim 20, wherein the concentration of chromium ion in the composition is from 100 to 600 ppm.

22. A composition according to claim 1 wherein the cross linking/retardant system additionally contains water or pyridine.

* * * * *